US007695714B2

(12) United States Patent
Kiss (10) Patent No.: US 7,695,714 B2
(45) Date of Patent: Apr. 13, 2010

(54) USE OF ALKALINE PHOSPHATASE TO MAINTAIN HEALTHY TISSUE MASS IN MAMMALS

(75) Inventor: Zoltan Kiss, Austin, MN (US)

(73) Assignee: Zoltan Laboratories LLC, Austin, MN (US)

( * ) Notice: Subject to any disclaimer, the term of this patent is extended or adjusted under 35 U.S.C. 154(b) by 714 days.

(21) Appl. No.: 11/463,022

(22) Filed: Aug. 8, 2006

(65) Prior Publication Data

US 2007/0148155 A1    Jun. 28, 2007

Related U.S. Application Data

(60) Provisional application No. 60/754,374, filed on Dec. 28, 2005.

(51) Int. Cl.
*A61K 38/46* (2006.01)

(52) U.S. Cl. .................................................... 424/94.6

(58) Field of Classification Search ....................... None
See application file for complete search history.

(56) References Cited

U.S. PATENT DOCUMENTS

| 7,011,965 B2 | 3/2006 | Kiss |
| 7,014,852 B2 | 3/2006 | Kiss |
| 7,048,914 B2 | 5/2006 | Kiss |
| 2004/0115185 A1 | 6/2004 | Kiss |
| 2005/0048046 A1 | 3/2005 | Kiss |

OTHER PUBLICATIONS

Samuels S.E. et al. Protein metabolism in the small intestine during cancer cachexia and chemotherapy in mice, Cancer Research, Sep. 1, 2000, vol. 60, pp. 4968-4974, entire document.*
Fuchs J. et al. Comparative activity of cisplatin, ifosfamide, doxarubicin, carboplatin, and etoposide in heterotransplanted hepatoblastoma, Cancer, Dec. 1, 1998, vol. 83, pp. 2400-2407, entire document.*
Morley et al. (2001), "Sarcopenia," *J. Lab. Clin. Med.* 137, 231-243.
van Leeuwen at al. (2003), "The embedded tumour: host physiology is important for the evaluation of tumour growth," *Br. J. Cancer* 89, 2254-2263.
Li et al. (2003), "Betacellulin improves glucose metabolism by promoting conversion of intraislet precursor cells to β-cells in streptozotocin-treated mice," *Am. J. Physiol. Endocrinol. Metab.* 285, E577-E583.
Baracos (2001), "Management of muscle wasting in cancer-associated cachexia," *Cancer* 92, 1669-1677.
Chen (2001), "Overexpression of metallothionein in pancreatic β-cells reduces streptozotocin-induced DNA damage and diabetes," *Diabetes* 50, 2040-2046.
Powis et al. (2000), "The role of the redox protein thioredoxin in cell growth and cancer," *Free Radical Biol. Med.* 29, 312-322.
Barton-Davis et al, (1998), "Viral mediated expression of insulin-like growth factor I blocks the aging-related loss of skeletal muscle function," *Proc. Natl. Acad. Sci. USA* 95, 15603-15607.

Owino et al. (2001), "Age-related loss of skeletal muscle function and the inability to express the autocrine form of insulin-like growth factor-1 (MGF) in response to mechanical overload," *FEBS Lett.* 505, 259-263.
Barbieri et al. (2003), "Chronic inflammation and the effect of IGF-1 on muscle strength and power in older persons," *Am. J. Physiol. Endocrinol. Metab.* 284, E481-E487.
De Benedetti et al. (1997), "Interleukin 6 causes growth impairment in transgenic mice through a decrease in insulin-like growth factor-I,". *J. Clin. Invest.* 99, 643-650.
O'Connor et al. (2002), "Insulin and amino acids independently stimulate skeletal muscle protein synthesis in neonatal pigs," *Am. J. Physiol. Endocrinol. Metab.* 284, E110-E119.
Anthony (2001), "Signaling pathways involved in translational control of protein synthesis in skeletal muscle by leucine," *J. Nutr.* 131, 856S-860S.
Yarasheski et al. (1995), "Effect of growth hormone and resistance exercise on muscle growth and strength in older men," *Am. J. Physiol. Endocrinol. Metab.* 268, E268-E276.
Ferrando et al. (2002), "Testosterone administration to older men improves muscle function: molecular and physiological mechanisms," *Am. J. Physiol. Endocrinol. Metab.* 282, E601-E607.
Seale et al. (2001), "The potential of muscle stem cells," *Develop. Cell* 1, 333-342.
Millan (1995), "Biology of human alkaline phosphatases with special reference to cancer," *Critical Reviews in Clinical Sciences* 32, 1-39.
She et al, (2000), "Growth factor-like effects of placental alkaline phosphatase in human fetus and mouse embryo fibroblasts," FEBS Letters, 468, 163-167.
She et al. (2000), "Placental alkaline phosphatase, insulin, and adenine nucleotides or adenosine synergistically promote long-term survival of serum-starved mouse embryo and human fetus fibroblasts," *Cellular Signaling* 12, 659-665.
U.S. Appl. No. 10/653,622, filed Sep. 2, 2003, entitled "Use of Placental Alkaline Phosphatase to Promote Skin Cell Proliferation".
Kozlenkov et al. (2002), "Function assignment to conserved residues in mammalian alkaline phosphatases," *J. Biol. Chem.* 277, 22992-22999.
Beck et al. (1994), "Expression of human placental alkaline phosphatase in *Escherichia coli*," *Protein Expression and Purification* 5, 192-197.

(Continued)

*Primary Examiner*—Irene Marx
*Assistant Examiner*—Satyendra K Singh
(74) *Attorney, Agent, or Firm*—Faegre & Benson LLP (57) ABSTRACT

Embodiments of the present invention relate to the use of placental alkaline phosphatase, and other members of the alkaline phosphatase family, to enhance protein synthesis in the muscle as well as the survival of non-cancerous differentiated cells in the muscle, adipose and other tissues. The ability of alkaline phosphatase to selectively enhance the survival of healthy cells and increase protein synthesis has many therapeutic applications. The use of alkaline phosphatase may prevent the loss of body weight and muscle mass typically experienced by diseased (such as cancer) or aging patients, or developing fetuses subjected to harmful conditions, or by patients who are treated with a toxic therapy including chemotherapy.

17 Claims, 7 Drawing Sheets

OTHER PUBLICATIONS

Heimo et al. (1998), "Human placenta alkaline phosphatase: Expression in *Pichia pastoris*, purification and characterization of the enzyme," *Protein Expression and Purification* 12, 85-92.

Carroll et al. (2004), "Combined growth hormone/insulin-like growth factor I in addition to glutamine-supplemented TPN results in net protein anabolism in critical illness," *Am. J. Physiol. Endocrinol. Metab.* 286, E151-E157.

Chang et al. (1990), "Modification of human placental alkaline phosphatase by periodate-oxidized 1,$N^6$-ethenoadenosine monophosphate," *Biochem. J.* 272, 683-690.

Carmichael et al. (1987), "Evaluation of tetrazolium-based semiautomated colorimetric assay: Assessment of chemosensitivity testing," *Cancer Res.* 47, 936-942.

Lynch et al, (2002), "Leucine is a direct-acting nutrient signal that regulates protein synthesis in adipose tissue," *Am. J. Physiol. Endocrynol. Metab.* 283, E503-E513.

Notification of Transmittal of the International Search Report and the Written Opinion for International Application No. PCT/US2006/030753, mailed Mar. 30, 2007 (6 pages).

* cited by examiner

USE OF ALKALINE PHOSPHATASE TO MAINTAIN HEALTHY TISSUE MASS IN MAMMALS

REFERENCE TO RELATED APPLICATION

This application claims priority from U.S. provisional application Ser. No. 60/754,374, filed Dec. 28, 2005.

FIELD OF THE INVENTION

Embodiments of this invention relate to the use of an alkaline phosphatase, such as placental alkaline phosphatase ("PALP"), to maintain muscle and adipose tissue mass in aging or diseased humans, who may or may not be treated with weight loss-inducing therapies. Alkaline phosphatase achieves these effects by enhancing protein synthesis in the muscle as well as the viability of differentiated muscle cells and adipocytes, and by extension of other types of healthy cells, in the corresponding healthy tissues. These protective effects of alkaline phosphatase can help normal tissues and the whole organism to withstand the destructive influence of tumors, cancer therapy, or other weight loss-inducing conditions.

BACKGROUND

One cause of disability, particularly in elderly people, is muscular atrophy or the loss of muscle mass, also known as sarcopenia. Aging-related muscular atrophy partly reflects impaired protein synthesis and activation of catabolism [Morley, J. E., Baumgartner, R. N., Roubenoff, R., Mayer, J. and Nair, K. S. (2001), "Sarcopenia," J. Lab. Clin. Med. 137, 231-243]. Critical illness, including advanced cancer, poorly controlled type 1 diabetes, trauma, sepsis, extensive burn injury, major surgery, and muscular dystrophy are also associated with muscular atrophy.

Cancer patients often experience cachexia characterized by a progressive decrease in both adipose tissue and skeletal muscle mass [van Leeuwen, I. M. M., Zonnefeld, C. and Kooijman, S. (2003), "The embedded tumour: host physiology is important for the evaluation of tumour growth," Br. J. Cancer 89, 2254-2263]. Natural toxins, such as streptozotocin (STZ), radiotherapy, and various chemotherapies, such as cisplatin (CisPt), doxorubicin, mytomycin C and etoposide, also seem to induce reduction in the muscle and adipose tissue mass [Li, L., Seno, M., Yamada, H. and Kojima, I. (2003), "Betacellulin improves glucose metabolism by promoting conversion of intraislet precursor cells to β-cells in streptozotocin-treated mice," Am. J. Physiol. Endocrinol. Metab. 285, E577-E583; Baracos, V. R. (2001), "Management of muscle wasting in cancer-associated cachexia," Cancer 92, 1669-1677; Chen, H., Carlson, E. C., Pellet, L., Moritz, J. T. and Epstein, P. N. (2001), "Overexpression of metallothionein in pancreatic β-cells reduces streptozotocin-induced DNA damage and diabetes," Diabetes 50, 2040-2046]. It is thought that these agents exert their toxic effects via generation of reactive oxygen species or ROS [Powis, G., Mustacich, D. and Coon, A. (2000), "The role of the redox protein thioredoxin in cell growth and cancer," Free Radical Biol. Med. 29, 312-322].

There are several known factors that prevent loss of muscle and adipose tissue. Insulin-like growth factor-1 (IGF-1) appears to play a key role in preventing muscle atrophy [Barton-Davis, E. R., Shoturma, D. I., Musaro, A., Rosenthal, N. and Sweeney, H. L. (1998), "Viral mediated expression of insulin-like growth factor I blocks the aging-related loss of skeletal muscle function," Proc. Natl. Acad. Sci. USA 95, 15603-15607]. However, during aging the muscle becomes unable to express the autocrine form of IGF-1 in response to mechanical overload resulting in reduced skeletal muscle function [Owino, V., Yang, S. Y. and Goldspink, G. (2001), "Age-related loss of skeletal muscle function and the inability to express the autocrine form of insulin-like growth factor-1 (MGF) in response to mechanical overload," FEBS Lett. 505, 259-263]. In addition, interleukin-6 (IL-6), a cytokine which plays a central role in inflammation, reduces both the level of circulating IGF-1 and the action of IGF-1 on muscle [Barbieri, M., Ferrucci, L., Ragno, E., Corsi, A., Bandinelli, S., Bonafe, M., Olivieri, F., Giovagnetti, S., Franceschi, C., Guralnik, J. M. and Paolisso, G. (2003), "Chronic inflammation and the effect of IGF-1 on muscle strength and power in older persons," Am. J. Physiol. Endocrinol. Metab. 284, E481-E487; De Benedetti, F., Alonzi, T., Moretta, A., Lazzaro, D., Costa, P., Poli, V., Martini, A., Ciliberto, G. and Fattori, E. (1997), "Interleukin 6 causes growth impairment in transgenic mice through a decrease in insulin-like growth factor-I," J. Clin. Invest. 99, 643-650]. Insulin and amino acids, particularly leucine, also seem to play a key role in preventing muscle loss by enhancing protein synthesis [O'Connor, P. M., Bush, J. A., Suryawan, A., Nguyen, H. V. and Davis, T. A. (2002), "Insulin and amino acids independently stimulate skeletal muscle protein synthesis in neonatal pigs," Am. J. Physiol. Endocrinol. Metab. 284, E110-E119; Anthony, J. C., Anthony, T. G., Kimball, S. R. and Jefferson, L. S. (2001), "Signaling pathways involved in translational control of protein synthesis in skeletal muscle by leucine," J. Nutr. 131, 856S-860S]. These, along with additional factors such as growth hormone, testosterone, and resistance exercise, increase metabolism as well as muscle growth and muscle strength [Yarasheski, K. E., Zachwieja, J. J., Campbell, J. A. and Bier, D. M. (1995), "Effect of growth hormone and resistance exercise on muscle growth and strength in older men," Am. J. Physiol. Endocrinol. Metab. 268, E268-E276; Ferrando, A. A., Sheffield-Moore, M., Yeckel, C. W., Gilkison, C., Jiang, J., Achacosa, A., Lieberman, S. A., Tipton, K., Wolfe, R. R. and Urban, R. J. (2002), "Testosterone administration to older men improves muscle function: molecular and physiological mechanisms," Am. J. Physiol. Endocrinol. Metab. 282, E601-E607].

Unfortunately, for many patients with debilitating diseases, many of the known therapies used to prevent the loss of muscle and adipose tissue are not ideal. IGF-1 and insulin levels may increase the risk of developing cancer and hypoglycemia after prolonged use. Similarly, growth hormone and testosterone have side effects that make them less than ideal. Nutrition-based therapies also do not significantly help maintenance of muscle mass and body weight.

There are several degenerative diseases of the skeletal muscle, including various forms of muscular dystrophy, that may be treated through transplantation of myoblasts and stem cells [Seale, P., Asakura, A., and Rudnicki, M. A. (2001), "The potential of muscle stem cells," Develop. Cell 1, 333-342]. Cell-based therapy may also be used to repair damaged skeletal muscle. However, as yet these procedures are limited by a short supply of myoblasts and stem cells and other technical difficulties including ensuring sterility of cell preparations. Therefore, promotion of survival of healthy cells and reversal of protein loss seem to be more viable strategies, particularly in combination, to prevent deterioration of healthy tissues in diseased and treated subjects.

SUMMARY OF THE INVENTION

Embodiments of the present invention generally relate to the use of placental alkaline phosphatase ("PALP"), and other members of the alkaline phosphatase family, to prevent deterioration and enhance survival of cells in the muscle and adipose tissue as well as other healthy tissues. The terms of both PALP and alkaline phosphatase are used interchangeably throughout the application, because other members of the alkaline phosphatase family may be used instead of PALP.

The ability of PALP to selectively enhance the survival of healthy cells has many therapeutic applications. It can be used to prevent weight loss typically experienced by diseased or aging patients, or by patients who are treated with a toxic therapy. As the final result of combined protective effects on healthy tissues, patients treated with PALP are expected to live longer than without such treatment. PALP may also be used to protect developing tissues in a fetus exposed to a harmful hormonal imbalance or an inadequate nutrient supply.

In one embodiment, the invention provides a method of decreasing or preventing the loss of weight in a mammal with a weight loss-inducing condition by administering an alkaline phosphatase or an active derivative. The weight loss-inducing condition may include cancer, chemotherapy, type 1 diabetes, trauma, sepsis, extensive burn injury, surgery, and muscular dystrophy. In another embodiment, the mammal may include a human fetus and the weight loss-inducing condition may include a hormonal imbalance or an inadequate supply of nutrients.

In another embodiment, the invention includes a method of decreasing the loss of weight in an aging mammal by administering an alkaline phosphatase or an active derivative.

In still another embodiment, the invention includes a method of decreasing the loss of weight in a mammal receiving weight loss-inducing therapy by administering an alkaline phosphatase or an active derivative. In this embodiment, the weight loss-inducing therapy may include, for example, chemotherapy or ROS-inducing therapies.

In yet another embodiment, the invention includes a method of treatment of cancer by periodically administering an alkaline phosphatase or an active derivative.

In a further embodiment, the invention provides the manufacture of a medicament to reverse weight loss induced by a disease or treatment.

In one embodiment, the mammal is administered a therapeutically effective amount of an alkaline phosphatase. The term "therapeutically effective amount" is used in this application to mean a dose that is effective in decreasing the loss of muscle and adipose tissue mass evidenced by decreased weight loss. Decreased weight loss may include weight gain, maintenance of weight, or a slower decrease in weight compared to patients that do not receive PALP. As used herein, the term "PALP" and the phrase "human PALP" is used interchangeably with PALP. The term "active PALP" is used in this application to refer to the human protein and its glycosylated and non-glycosylated forms as well as peptides derived from these proteins. The terms "substantially purified" and "highly purified" are used herein to encompass preparations of PALP that are obtained from a raw extract by one or more purification steps, such as, for example, solvent extraction, column chromatography separation, or other separation methods. These methods may enrich the concentration of PALP, relative to the raw extract, to an extent that PALP is highly concentrated, and the remaining components do not pose any significant health risk and do not reduce the beneficial effects of PALP. The terms "substantially purified" and "highly purified" should not be construed to connote absolute purity.

As used herein the phrase "body weight loss condition" refers to the loss of body weight and muscle mass because of aging, weight loss-inducing therapy, weight loss-inducing condition, cancer or any treatment associated with body weight loss. The PALP used may be obtained by extraction from natural sources, chemically synthesized or by recombinant methods.

DETAILED DESCRIPTION OF THE INVENTION

In embodiments of this invention, PALP or another alkaline phosphatase may be used to enhance survival of differentiated skeletal muscle cells and adipocytes (fat cells) as well as epithelial cells derived from human mammary tissue. In addition, PALP may also be used to reduce the loss of body weight induced by three different factors: (i) the ROS-inducing agent streptozotocin (STZ) that selectively destroys insulin-producing β-cells, (ii) large tumors, and (iii) chemotherapy. Accordingly, PALP may be used to increase the survival of diseased mammals, particularly humans, by protecting the vital functions of organs without affecting or even weakening the tumor tissues and other diseased tissues.

The Active Component

PALP is one of the presently known four members of the alkaline phosphatase enzyme family that hydrolyzes phosphate-containing compounds at alkaline pH [J. L. Millan, and W. H. Fishman (1995), "Biology of human alkaline phosphatases with special reference to cancer," Critical Reviews in Clinical Sciences 32, 1-39]. Other members of this phosphatase group that also hydrolyze phosphate-containing compounds at alkaline pH include the tissue non-specific (liver/bone/kidney), the intestinal, and PALP-like (germ-cell) alkaline phosphatases. Mature PALP is a dimer of two identical glycosylated subunits. Each subunit has an approximate molecular weight of 66 kDa, as determined by gel electrophoresis. It has been shown to have several cellular effects. Thus, PALP enhanced both the proliferation and survival of mouse embryo fibroblasts and fibroblast-like cells derived from the lung of human fetus [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," FEBS Letters, 468, 163-167; Q.-B. She, J. J. Mukherjee, T. Chung, and Z. Kiss (2000), "Placental alkaline phosphatase, insulin, and adenine nucleotides or adenosine synergistically promote long-term survival of serum-starved mouse embryo and human fetus fibroblasts," Cellular Signaling 12, 659-665]. PALP also enhanced proliferation of human fibroblasts [U.S. Pat. No. 7,011,965, entitled "Compositions and methods for stimulating wound healing and fibroblast proliferation; U.S. patent application Ser. No. 10/653,622, filed Sep. 2, 2003 and entitled "Use of Placental Alkaline Phosphatase to Promote Skin Cell Proliferation," incorporated herein by reference]. In addition, in obese and diabetic mice PALP was found to lower blood glucose level and decrease body weight while it increased body weight in type 1 diabetic animals [U.S. Pat. No. 7,014,852, entitled "Alkaline phosphatase to induce weight loss or reduce weight gain", and U.S. Pat. No. 7,048,914, entitled "Placental alkaline phosphatase to control diabetes", incorporated herein by reference]. Finally, as suggested by the experiments presented in embodiments of this invention, PALP may be useful to decrease the toxic side effects of anti-cancer treatments such as treatment with cisplatin, thus prolonging the life of cancer patients.

All human alkaline phosphatase enzymes have comparable phosphatase activity. Also, these proteins bind to the same structure in the cell membrane (glycosylphosphatidylinositol or GPI anchor). Finally, the contribution of phosphatase activity of PALP to its protective effects on normal cells is likely.

It may be possible to synthesize or develop an active derivative that is a smaller fragment of a PALP amino acid sequence and demonstrates efficacy similar to that of native PALP. It has been demonstrated that alkaline phosphatase activity is not required in native PALP to stimulate mitogenesis. For example, both digestion of PALP with the protease bromelain and elimination of alkaline phosphatase activity through mutation provided an active derivative with respect to cell proliferation [U.S. patent application Ser. No. 10/653,622, filed Sep. 2, 2003 and entitled "Use of Placental Alkaline Phosphatase to Promote Skin Cell Proliferation"; Pub. No. US 2005/0048046 A1, Pub. date, Mar. 3, 2005].

Therefore, it may be possible to synthesize or develop an active derivative that is a smaller fragment of a PALP amino acid sequence but still demonstrates efficacy similar to that of native PALP. For example an active derivative may be formed by exchanging amino acids at critical sites, by modifying a PALP amino acid sequence or a sequence of smaller PALP peptides. Likewise, chemical or enzymatic changes in the level and position of glycosylation may maintain or enhance the effects of PALP or its derivatives. In the practice of embodiments of this invention, modified PALP, smaller PALP-derived peptides, or modified PALP-derived peptides may be similarly effective or even more effective than native PALP. Each of these is considered to be active derivatives. In embodiments of the present invention, native glycosylated PALP and its active derivatives as well as non-glycosylated PALP and its active derivatives may be used.

Alkaline Phosphatase-Containing Compositions

Preparations of PALP for use in embodiments of the invention may be prepared using a variety of methods. Human PALP, commercially available from Sigma-Aldrich (St. Louis, Mo.; catalog number P3895; CAS Registry Number 9001-78-9) or Calbiochem (San Diego, Calif.; catalog number 524604) may be used. These commercially available preparations often contain impurities that may be removed using known purification methods before it is administered to a patient. However, if the commercially available PALP includes a therapeutically effective amount of PALP and the impurities do not interfere with the beneficial effects of the PALP, the commercially available PALP may not need to be purified before it is administered to a patient.

Human PALP, and particularly a smaller molecular weight active PALP derivative, may also be obtained by chemical synthesis using conventional methods. For example, solid-phase synthesis techniques may be used to obtain PALP or an active derivative.

Recombinant methods of obtaining suitable preparations of PALP or active PALP derivatives are also suitable. Using the cDNA of PALP, recombinant protein may be produced by one of the many known methods for recombinant protein expression. PALP has been cloned and expressed in cells as described by Kozlenkov, et al. [Kozlenkov, A., Manes, T., Hoylaerts, M. F. and Millan, J. L. (2002), "Function assignment to conserved residues in mammalian alkaline phosphatases," J. Biol. Chem. 277, 22992-22999]. Production of recombinant PALP by bacteria [Beck, R. and Burtscher, H. (1994), "Expression of human placental alkaline phosphatase in *Escherichia coli*," Protein Expression and Purification 5, 192-197] and yeast [Heimo, H., Palmu, K. and Suominen, I. (1998), "Human placenta alkaline phosphatase: Expression in *Pichia pastoris*, purification and characterization of the enzyme," Protein Expression and Purification 12, 85-92 is also a suitable method of obtaining PALP for use with the method of the present invention.

A suitable preparation of PALP, and particularly an active PALP derivative, may be also obtained by chemical synthesis using conventional methods. For example, solid phase synthesis techniques may be used to obtain PALP or an active derivative.

A preparation of human PALP may also be obtained by extraction from placental tissue. Human placenta synthesizes the enzyme during pregnancy so that toward the end of the third term, the level of PALP in the placenta tissue and the maternal and fetal blood becomes very high. Therefore, a preparation of PALP may be obtained by butanol extraction of homogenized placenta. Other methods of extraction from placental tissue are also suitable.

As with the commercially available human PALP, it may be suitable to purify the raw placental extracts of PALP before using it in embodiments of the present invention. Raw placental extracts may contain other proteins, lipids, proteolipids, carbohydrates, metals, vitamins, and the like that may cause unexpected side effects when administered to a patient.

Therefore, it may be suitable to use a known purification method to remove these contaminants from the raw placental extract.

Raw extracts of PALP may also be treated to purify or concentrate the amount of PALP in the preparation. In some raw extracts of PALP, the relative concentration of PALP may be too low to result in the required biological effect. Purified and concentrated PALP may be suitable for treatment in vivo to ensure the quality of the preparation and to exclude the health risks caused by unidentified contaminants. Thus purified preparations of PALP may have a much higher concentration of the active component than found in a raw tissue extract. Substantially purified preparations of bone-specific, tissue non-specific, and PALP-like (germ) alkaline phosphatase enzymes are all available commercially (for example, from Sigma-Aldrich).

The stimulatory effects of PALP on fibroblast proliferation in vitro may be enhanced by pre-heating it at 65-75° C. for 30 min [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," FEBS Letters, 468, 163-167]. Thus, a step of heat-activation may be included during the final preparation of PALP for injection.

Methods of Treatment

PALP may be administered by a variety of methods "for the treatment of weight loss due to, for example, a weight loss-inducing condition, aging, weight loss-inducing therapy and cancer." In one embodiment, a PALP solution is administered to the mammal or human by injection. Any suitable method of injection, such as intravenous, intraarterial, intramuscular, intraperitoneal, intraportal, intradermal or subcutaneous may be used. The mode of injection may be selected to provide either local delivery (such as intradermal, partly subcutaneous, or intraportal application), or delivery to the cancers of internal organs via blood (such as intravenous, intraarterial, intraperitoneal and subcutaneous applications). Local delivery may provide more efficient protection for the normal tissues adjacent to tumor tissue. Another method for local delivery is direct injection into the diseased tissue, such as cancer. For example, in case of breast cancer, direct (intratumoral) application may simultaneously inhibit tumor growth and enhance survival of adjacent normal tissues. PALP may also be directly injected into the skeletal muscle.

For injection of a solution of PALP or another alkaline phosphatase, the protein may be dispersed in any physiologically acceptable carrier that does not cause an undesirable physiological effect. Examples of suitable carriers include physiological saline and phosphate-buffered saline. The injectable solution may be prepared by dissolving or dispersing a suitable preparation of the active protein component in the carrier using conventional methods. As examples only, a suitable composition for the practice in the methods include an alkaline phosphatase in a 0.9% physiological salt solution to yield a total protein concentration of 10 mg/ml. Another suitable solution includes PALP in a 0.9% physiological salt solution to yield a total protein concentration of 20 mg/ml. A third solution includes PALP in a 0.9% physiological salt solution to yield a total protein concentration of 50 mg/ml. Alternatively, PALP may be enclosed in liposomes such as immunoliposomes, or other delivery systems or formulations that are known in the art.

A suitable dosage for systemic administration for the treatment of weight-loss due to, for example, a weight loss-inducing condition, aging, weight loss-inducing therapy and cancer may be calculated in grams of the active agent(s) per square meter of body surface area for the subject. In one embodiment, the therapeutically effective amount of PALP is between about 0.01 to 2.5 g of alkaline phosphatase per $m^2$ body surface of the mammal. In another embodiment, the therapeutically effective amount of PALP is between 0.1 to 1 g per $m^2$ body surface of the mammal.

In one embodiment, the therapeutically effective amount of PALP may be administered once daily. In another embodiment, the dose is administered twice or three times weekly. In still another embodiment, administration is performed once a week or biweekly. Since the half-life time of PALP and other alkaline phosphatases is relatively long (4-6 days), one suitable application is twice a week or once a week. Another factor to consider when determining the effective amount is whether alkaline phosphatase is used alone or used as part of a more complex regimen involving other treatments. For example, if a patient is simultaneously or alternatively treated with both PALP and another therapy, the effective tolerated amount of the former may be less compared to a regimen when the subject is treated with PALP alone.

The stimulatory effects of PALP on fibroblast proliferation in vitro is enhanced by pre-heating it at 65-75° C. for 30 minutes [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," FEBS Letters, 468, 163-167]. Thus, a step of heat-activation may be included during the final preparation of PALP for injection.

The stimulatory effect of PALP on fibroblast proliferation in vitro is also enhanced by adding calcium and zinc to the medium [Q.-B. She, J. J. Mukherjee, J.-S. Huang, K. S. Crilly, and Z. Kiss (2000), "Growth factor-like effects of placental alkaline phosphatase in human fetus and mouse embryo fibroblasts," FEBS Letters, 468, 163-167]; it is expected that these cations also enhance the effects of PALP on cell survival. Accordingly, the final preparation of PALP for injection may include 1-3 mM of a calcium compound (for example, calcium chloride) and/or 1-50 µM of a zinc compound (for example, zinc chloride or zinc sulfate).

The injectable solution may be modified by an additive or enhancer that positively influences the proliferation and survival of normal tissues. Examples of such additives and enhancers include IGF-1, and other growth factors that protect against muscle atrophy [Barton-Davis, E. R., Shoturma, D. I., Musaro, A., Rosenthal, N. and Sweeney, H. L. (1998), "Viral mediated expression of insulin-like growth factor I blocks the aging-related loss of skeletal muscle function," Proc. Natl. Acad. Sci. USA 95, 15603-15607], insulin and amino acids, particularly leucine, which enhance protein synthesis in the muscle and adipose tissue through different mechanisms [O'Connor, P. M., Bush, J. A., Suryawan, A., Nguyen, H. V. and Davis, T. A. (2002), "Insulin and amino acids independently stimulate skeletal muscle protein synthesis in neonatal pigs," Am. J. Physiol. Endocrinol. Metab. 284, E110-E119; Anthony, J. C., Anthony, T. G., Kimball, S. R. and Jefferson, L. S. (2001), "Signaling pathways involved in translational control of protein synthesis in skeletal muscle by leucine," J. Nutr. 131, 856S-860S; Lynch, C. J., Patson, B. J., Anthony, J., Vaval, A., Jefferson, L. S. and Vary, T. C. (2002), "Leucine is a direct-acting nutrient signal that regulates protein synthesis in adipose tissue," Am. J. Physiol. Endocrynol. Metab. 283, E503-E513], growth hormone [Yarasheski, K. E., Zachwieja, J. J., Campbell, J. A. and Bier, D. M. (1995), "Effect of growth hormone and resistance exercise on muscle growth and strength in older men," Am. J. Physiol. Endocrinol. Metab. 268, E268-E276], and testosterone [Ferrando, A. A., Sheffield-Moore, M., Yeckel, C. W., Gilkison, C., Jiang, J., Achacosa, A., Lieberman, S. A., Tipton, K., Wolfe, R. R. and Urban, R. J. (2002), "Testosterone administration to older men improves muscle function: molecular and physiological mechanisms," Am. J. Physiol. Endocrinol. Metab. 282, E601-E607]. In addition, PALP may be administered together with nutrition-based therapies or combined growth hormone/IGF-1/nutritional therapy [Carroll, P. V., Jackson, N. C., Russell-Jones, D. L., Treacher, D. F., Sonksen, P. H. and Umpleby, A. M. (2004), "Combined growth hormone/insulin-like growth factor I in addition to glutamine-supplemented TPN results in net protein anabolism in critical illness," Am. J. Physiol. Endocrinol. Metab. 286, E151-E157] to enhance protein anabolism in critical illness. Similarly, PALP may be used together with insulin to prevent weight loss in type 1 diabetic patients. Because PALP is the primary agent in the above therapies, the concentrations of these additives and enhancers may be lowered to a level that still increases the effects of PALP but exerts no serious side effects.

EXAMPLES

Example 1

Purification and Spectrophotometric Assay of PALP

Human PALP (Type XXIV, 1020 units of total activity) in a partially purified form was obtained commercially from Sigma-Aldrich. A butanol extraction of placental tissue, followed by one or more chromatographic steps, was performed by Sigma-Aldrich to obtain the partially purified material.

Figure 1:
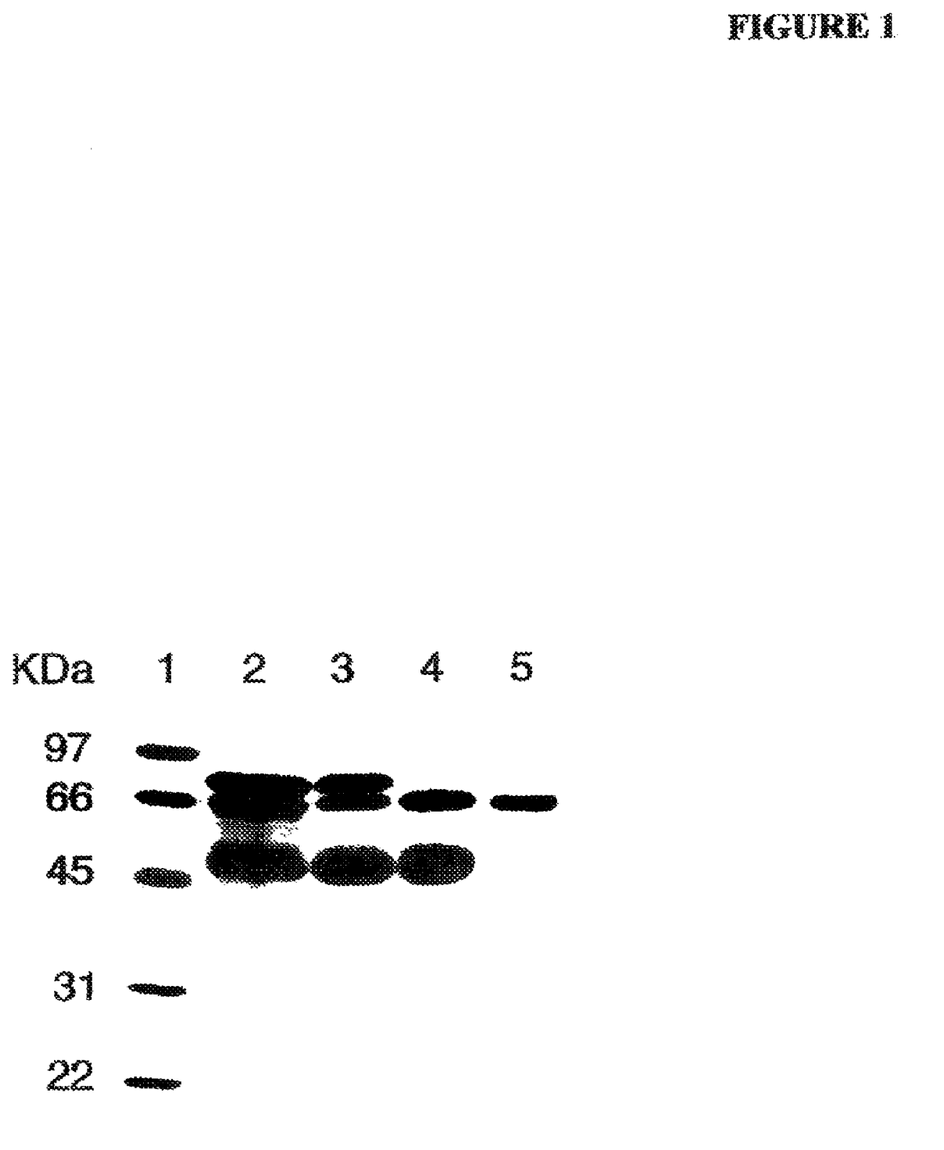
FIG. 1 shows a digital image of a gel separation, demonstrating that the PALP used for the animal and in vitro experiments, except when indicated otherwise, was homogeneous or near homogeneous.

As determined by sodium dodecyl sulfate-polyacrylamide gel electrophoresis (SDS-PAGE), the partially purified PALP obtained from Sigma-Aldrich (denoted "commercial PALP" herein) was not homogeneous and contained other proteins. FIG. 1 shows a digital image of a gel separation of a preparation comprising commercial PALP without further purification, and other preparations of PALP of increasing purity. Separation of proteins was performed by conventional SDS-PAGE, and proteins were stained with coomassie blue stain. Lane 1 contains various molecular mass standards for comparison. Lane 2 represents a preparation containing commercial PALP with a strong 52 kDa band representing AT and another strong 66-68 kDa band representing a mixture of PALP and albumin. Lanes 3 and 4 represent preparations comprising commercial PALP material after further purification steps (described below), and lane 5 represents a preparation of homogeneous PALP obtained by the complete purification procedure described below.

A purification procedure was performed to further purify the commercially obtained PALP to homogeneity. A slightly modified procedure described earlier [She, Q.-B., Mukherjee, J. J., Huang, J.-S., Crilly, K. S. and Kiss, Z. (2000), "Growth factor-like effects of placental alkaline phosphatase in human and mouse embryo fibroblasts," FEBS Lett. 469, 163-167] was used which are incorporated by reference.

The solution of commercial PALP was prepared by dissolving 350 mg of commercial PALP into 10 ml of buffer A (0.1 M sodium acetate, 0.5 M NaCl, 1 mM $MgCl_2$, 1 mM $CaCl_2$, adjusted to pH 6.5). This solution was then further purified by successive Concanavalin A-Sepharose and Q-Sepharose chromatography as indicated earlier by Chang et al. Chang, T.-C., Huang, S.-M., Huang, T.-M. and Chang, G.-G. (1992), "Human placenta alkaline phosphatase: An improved purification procedure and kinetic studies," Eur. J. Biochem. 209, 241-247 followed by t-butyl hydrophobic interaction chromatography as described by She et al [She, Q.-B., Mukherjee, J. J., Huang, J.-S., Crilly, K. S. and Kiss, Z. (2000), "Growth factor-like effects of placental alkaline phosphatase in human and mouse embryo fibroblasts," FEBS Lett. 469, 163-167] except that this last step was repeated in about 60% of cases (to eliminate traces of contaminant protein) in the invention.

First, the PALP solution was passed through a Concanavalin A-Sepharose column followed by an elution step using buffer A (50 mM α-methyl-D-mannopyranoside) as solvent. The active fractions collected from the effluent were pooled and dialyzed against buffer B (50 mM Tris-HCL at pH 7.7). SDS-PAGE separation of the collected and dialyzed fraction is shown in FIG. 1 in lane 3.

The collected and dialyzed fraction from the previous step was then passed through a Q-Sepharose column. The fraction of interest was eluted with buffer B using a linear gradient of 0-250 mM potassium phosphate at a pH of 7.5. The active fractions from the Q-Sepharose column were pooled and dialyzed against phosphate-buffered saline and concentrated by Amicon ultrafiltration. SDS-PAGE separation of the collected and dialyzed fraction is shown in FIG. 1 in lane 4, which demonstrates that at least two major proteins are still present in the fraction after dialysis.

Then, the collected and dialyzed fraction from the previous step was purified to homogeneity by t-butyl hydrophobic interaction chromatography (HIC). Prior to adding the fraction to the t-butyl HIC column, the fraction was made 2 M in ammonium sulfate, and the pH was adjusted to 6.8. The 5-ml bed volume t-butyl HIC cartridge (BIO-RAD, Hercules, Calif.) was connected to a fast performance liquid chromatography (FPLC) system from PHARMACIA (Peapack, N.J.). The fraction was introduced to the HIC column, and the column was eluted with buffer C (100 mM sodium phosphate buffer, 2 M ammonium sulfate at pH 6.8). The column was eluted with buffer C until a first protein-containing fraction completely eluted, and then a negative gradient of 2 M-to-0 M ammonium sulfate in 100 mM sodium phosphate at pH 6.8 was passed over the column. The negative linear gradient was used to elute a second protein-containing fraction, which contained the enzymatically active PALP protein.

The enzymatically active PALP fraction from the HIC separation was dialyzed against phosphate buffered saline and concentrated by Amicon ultrafiltration. The presence and purity of the PALP enzyme in the fraction was confirmed by SDS-PAGE. After electrophoretic separation, the gel was stained using coomassie blue or silver stain for visual observation of protein bands. When a single protein band with an approximate molecular weight of 66 kDa was not observed, the last chromatographic step was repeated. The pure PALP was further identified by sequence analysis performed by the Mayo Clinic Protein Core Facility (Rochester, Minn., US).

PALP enzyme activity was assayed using a spectroscopic method by monitoring the hydrolysis of 4-nitrophenylphosphate (as an increase in absorbance at 410 nm) at room temperature (22° C.) as described in Chang, G.-G., Shiao, M.-S., Lee, K.-R. and Wu, J.-J. (1990), "Modification of human placental alkaline phosphatase by periodate-oxidized 1,$N^6$-ethenoadenosine monophosphate," Biochem. J. 272, 683-690. Activity analysis of 5-10 μg purified enzyme was performed in 1 mL incubation volume containing 50 mM $Na_2CO_3$/$NaHCO_3$, 10 mM $MgCl_2$, 10 mM 4-nitrophenylphosphate at pH 9.8. The extinction coefficient of 4-nitrophenol was taken as $1.62 \times 10^4$ $M^{-1}$ $cm^{-1}$. An enzyme activity of 1 U (unit) is defined as 1 µmol substrate hydrolyzed/min at 22° C. at pH 9.8.

Example 2

Production of Recombinant PALP

Recombinant PALP was produced following a known procedure described in Kozlenkov, A., Manes, T., Hoylaerts, M. F. and Millan, J. L. (2002), "Function assignment to conserved residues in mammalian alkaline phosphatases," J. Biol. Chem. 277, 22992-22999, which is hereby incorporated by reference.

Example 3

Use of the MTT Assay to Determine Cell Viability

In the Examples below, an MTT assay was used to determine the relative number of viable cells after treatments in vitro. The steps of this assay are described in Carmichael, J, De Graff, W. G., Gazdar, A. F., Minna, J. D. and Mitchell, J. B. (1987), Evaluation of tetrazolium-based semiautomated colorimetric assay: Assessment of chemosensitivity testing," Cancer Res. 47, 936-942, which is hereby incorporated by reference. This colorimetric assay is based on the ability of living cells, but not dead cells, to reduce 3-(4,5-dimethyl thiazol-2-yl)-2,5-diphenyltetrazolium bromide. For this assay, cells were seeded in 96-well plates, and the MTT assay was performed as described in the above article both in untreated and treated cell cultures. The MTT assay also was performed at the time when the treatment was started to allow for assessment of the proliferation and survival rates in the control and treated cell cultures. Absorption was measured at wavelength 540, indicated in the Tables below as $A_{540}$. In the MTT assay, higher values mean proportionally higher numbers of viable cells.

Example 4

Cell Lines and Cell Culture Reagents

Fetal bovine serum (FBS), fetal calf serum (FCS), and all tissue culture media were obtained from Life Technologies (formerly GIBCO BRL) (Rockville, Md.). The MCF-7 estrogen receptor positive human breast cancer cells were derived from the National Institute of Health, Bethesda, Md. All other cell lines, as listed below, were provided by the American Type Culture Collection (Rockville, Md.).

MCF-7 cells and L6 skeletal muscle myoblasts (ATCC CRL1458) were cultured in Dulbecco's modified Eagle's medium (DMEM) supplemented with 10% FBS. Early passage (passages 6-10) L6 myoblasts were differentiated to the myotube stage by a standard procedure involving incubation of cells in 2% serum-containing medium for 8 days.

The 3T3-L1 mouse embryo preadipocyte cell line (ATCC CCL-92.1) was maintained in DMEM containing 10% FCS. Confluent cultures of 3T3-L1 cells were differentiated into adipocytes by a standard procedure which involves incubation of cells first for 3 days in 10% serum-containing medium supplemented with 500 nM insulin, 250 nM dexamethasone, and 0.5 mM isobutylmethylxanthine, followed by incubation for 3 days in the presence of 500 nM insulin (in 10% serum-containing medium), and then for another 3-4 day period in the presence of 10% serum only. By the end of the procedure about 90% of 3T3-L1 cells were converted into adipocytes.

The MCF-10A epithelial cell line (ATCC CRL-10317), established from the mammary tissue of a patient with fibrocystic breast disease, were maintained in 1:1 mixture of DMEM and Ham's F12 medium supplemented with 5% horse serum, 20 ng/ml epidermal growth factor, 100 ng/ml cholera toxin, 0.01 mg/ml insulin and 500 ng/ml hydrocortisone.

The AN3 CA human endometrial adenocarcinoma cell line (ATCC HTB 111) and CCD-966Sk human normal skin fibroblast line (ATCC CRL 1881) were maintained in Eagle's MEM supplemented with non-essential amino acids, 1 mM sodium pyruvate, Earle's BSS and 10% FBS.

The Caov-3 human ovarian adenocarcinoma cell line (ATCC HTB 75) was maintained in DMEM containing 10% FBS.

The ZR-75-1 human estrogen positive breast carcinoma cell line (ATCC CRL 1500) was maintained in RPMI 1640 containing 10% FBS.

The T-47D human estrogen positive breast carcinoma cell line (ATCC HTB 133) was maintained in RPMI 1640 containing 0.2 IU bovine insulin/ml and 10% FBS.

The human skin fibroblast cell line CCD 966 SK, derived from a 52-year-old subject, was maintained in 10% FBS-containing MEM. These cells were used between 4-7 passages before they started to senesce.

Example 5

Determination of Protein Synthesis from Radiolabeled Amino Acid in L6 Myotubes and Human Skin Fibroblasts The following radiolabeled amino acids were from Amersham Biosciences, Piscataway, N.J.; L-[2,3-$^3$H]alanine (TRK400), L-[G-$^3$H glutamine (TRK459), L-[4,5-$^3$H]leucine (TRK636), L-[methyl-$^3$H]methionine (TRK705, and L-[2,3-$^3$H]proline (TRK638]. L6 myoblasts were seeded into 12-well plates and incubated until the cultures reached about 50% confluence. Then the medium was changed to 1% serum-containing medium and incubations continued for 8 days (replacing the medium with fresh medium on day 4) to allow differentiation of most cells to the myotube stage. The medium was changed again to fresh 1% serum-containing medium followed by treatments with various PALP preparations for 24 hours. This was followed by the addition of respective radiolabeled amino acid (1.0 µCi/ml) for 4 hours in the continuous presence of PALP. PALP preparations and amino acids were dissolved in the medium and added to the incubation medium in 50-50-µl volume (final incubation volume: 0.75 ml). At the conclusion of incubations, the medium was rapidly collected, and the cells were washed with 3×3-ml serum-free medium (within 30 seconds). This was followed by the addition of 1-ml of ice-cold methanol/water mixture (98% methanol: 2% water) to extract free amino acids and precipitate proteins. A 0.8-ml volume of extract was added to 9-ml of Ecolume scintillation mixture (Amersham) and radioactivity was counted using a Beckman scintillation counter. To dissolve precipitated protein, 1-ml of 1 N NaOH was added to the wells. Then, a 0.8-ml aliquot of the mixture was transferred to a scintillation vial. The mixture was neutralized with 80-µl of 10 N HCL, followed by the addition of 10-mL Ecolume and counting of radioactivity. Protein synthesis in confluent cultures of CCD 966 SK human fibroblasts was measured as above with small modifications indicated in the legend to Table 5.

Example 6

Development and Treatment of Tumor Models

Tumors were developed in first generation hybrid BDF1 (C57 B1 female×DBA/2 male) adult female mice kept at specified pathogen free (SPF) hygienic level. HT-168 human melanoma, PC-3 human prostate adenocarcinoma, and MXT mouse mammary tumor pieces each with about 0.1 cm$^3$ volume were transplanted subcutaneously to develop the tumors. After 12-18 days when the tumor-bearing mice were used, the size of the tumors was in the 0.2-0.5 cm$^3$ range. All compounds used were dissolved in physiological (0.9%) saline (NaCl) and the agents, alone or in combinations, were applied subcutaneously or intaperitoneally in 50-μl volume. The volume of tumor was determined in three dimensions by using calipers. Tumor volume was calculated according to the generally accepted formula, $V=a^2 \times b \times \pi/6$, where "a" and "b" mean the shortest and longest diameter, respectively, of the measured tumor.

Examples Illustrating the Effects of PALP on Survival and Protein Synthesis in Differentiated L6 Myotubes.

Example 7

PALP Enhances Survival of Differentiated L6 Myotubes

In this example, L6 myotubes were used at about 65-70% confluence to determine the effect of PALP on their survival. In these experiments, the medium was changed to serum-free medium and incubations continued for 6 days in the absence of PALP or in the presence of purified PALP. Serum-free medium is often used in cell experiments to model the toxic environment that can occur in vivo. The data, shown in TABLE 1, are expressed as mean values ±std. dev. of 8 determinations. Such long-term incubation of myotubes in serum-free medium greatly reduced the number of viable cells. However, when these cells were incubated with PALP, the number of viable myotubes significantly increased.

Based on the data shown in TABLE 1 it is reasonable to expect that treatment of a mammal with alkaline phosphatase will provide protection against muscle cell death induced by disease or toxic treatment.

TABLE 1

PALP reduces serum-free medium-induced death of L6 myotubes.

| PALP | $A_{540}$ L6 myotubes |
|---|---|
| Control, 0 hour | 0.871 ± 0.034 |
| Control, 72 hours | 0.262 ± 0.044 |
| PALP, 15 μg/ml | 0.738 ± 0.053 |

Example 8

PALP Enhances Protein Synthesis in L6 Cells Myotubes

L6 myotubes were incubated with various radiolabeled amino acids to determine if purified PALP enhanced cellular uptake of amino acids and protein synthesis. The cells were first incubated with PALP (15 μg/ml) for 24 hours, followed by incubations in the continuous presence of PALP and radiolabeled amino acids for 4 hours. The data, shown in TABLE 2, are presented in units of disintegration per minute ("dpm"), a measurement of radioactive decay. Higher values indicate increased uptake of cellular amino acid and increase synthesis of proteins from the cellular amino acids. The data are mean values ±std. dev. of 3 independent determinations. In case of each amino acid, PALP enhanced incorporation of amino acids into the cellular free amino acid pool and cellular proteins by about 20%-37%. This suggests that PALP primarily increased cellular uptake of amino acids that then leads to increased protein synthesis.

Other experiments were also performed in which the incubation times were reduced. PALP had little or no effects on amino acid uptake and protein synthesis when the incubation time was 2, 5 or 12 hours (data not shown).

These results suggest that PALP may reverse the effects of agents or physiological conditions, such as cancer, that result in increased catabolism of muscle proteins in vivo. Taken together with data in TABLE 1, it is reasonable to expect that treatment of a mammal with PALP is suitable to prevent the loss of muscle mass induced by a disease or a toxic treatment.

TABLE 2

PALP stimulates amino acid uptake and protein synthesis in L6 myotubes.

| [$^3$H]Amino acid | [$^3$H]Free Cellular Amino Acid (dpm) | | [$^3$H]Total Cellular Protein (dpm) | |
|---|---|---|---|---|
| | None | PALP | None | PALP |
| Alanine | 51,670 ± 3,190 | 64,030 ± 2,680 | 40,730 ± 1,480 | 54,030 ± 2,670 |
| Glutamine | 29,743 ± 2,170 | 35,790 ± 1,620 | 8,020 ± 550 | 10,260 ± 520 |
| Leucine | 8,270 ± 150 | 10,060 ± 500 | 31,510 ± 1,980 | 42,940 ± 1,320 |
| Methionine | 9,350 ± 1,070 | 11,400 ± 650 | 25,540 ± 2,010 | 32,450 ± 1,620 |
| Proline | 24,820 ± 1,960 | 34,020 ± 2,250 | 25,110 ± 2,100 | 33,920 ± 3,320 |

Examples Illustrating the Effects of PALP on the Survival of Preadipocyte 3T3-L1 Cells.

Example 9

PALP Protects 3T3-L1 Cells in Serum-Free Medium

3T3-L1 cells were seeded into 96-well plates at 8,000 cells/well. After the cells reached confluence, the medium was replaced with serum-free medium followed by treatments with purified PALP and incubations for 6 days. The relative number of viable cells was determined by the MTT assay. The data, shown in TABLE 3, are expressed as mean values ±std. dev. of 4 determinations. The results indicate that during the 6 day period, 2.5-15 µg/ml concentrations of PALP provided protection against cell death induced by serum-free medium.

Surviving pre-adipocytes (such as 3T3-L1 cells) in the adipose tissue are expected to replace dead adipocytes that died as the consequence of a disease or a toxic treatment. Therefore, based on the data presented in TABLE 3, it is reasonable to expect that treatment of a mammal with PALP is suitable to prevent or reduce the loss of adipose tissue mass induced by a disease or a toxic treatment.

TABLE 3

PALP protects 3T3-L1 cells against serum-free medium-induced death.

| PALP | $A_{540}$ |
|---|---|
| Control, 0 day | 1,603 ± 0.125 |
| Control, 6 days | 0.225 ± 0.022 |
| PALP, 2 µg/ml, 72 hours | 0.574 ± 0.0.45 |
| PALP, 5 µg/ml, 72 hours | 0.840 ± 0.075 |
| PALP, 10 µg/ml, 72 hours | 1,510 ± 0.131 |
| PALP, 15 µg/ml, 72 hours | 1,647 ± 0.142 |

Example Illustrating PALP Stimulation of Protein Synthesis in Human Fibroblasts.

Example 10

Effects of PALP on Amino Acid Uptake and Protein Synthesis in CCD 966 Sk Human Fibroblasts Previously, it was already shown that PALP enhances proliferation of human fibroblasts [U.S. Pat. No. 7,011,965, entitled "Compositions and methods for stimulating wound healing and fibroblast proliferation; U.S. patent application Ser. No. 10/653,622, filed Sep. 2, 2003 and entitled "Use of Placental Alkaline Phosphatase to Promote Skin Cell Proliferation," incorporated herein by reference]. In the following experiment, the goal was to demonstrate that PALP also stimulates protein synthesis in a cell line, such as the CCD 966 human skin fibroblast line, which is unrelated to the muscle tissue. A positive finding was expected to indicate that stimulation of protein synthesis by PALP is not restricted to the skeletal muscle tissue.

CCD 966 fibroblasts were first incubated with PALP (15 µg/ml) for 24 hours, followed by incubations in the continuous presence of PALP and radiolabeled amino acids (1 µCi/well) for 5 hours. The data, shown in TABLE 4, are expressed as mean values ±std. dev. of 3 independent determinations. With each amino acid, PALP enhanced the incorporation of amino acids into the cellular free amino acid pool and cellular proteins. This indicates that PALP may be suitable to increase viability (not necessarily proliferation) of fibroblast cells. The results also provide a strong indication that the stimulatory effect of PALP on protein synthesis is not restricted to the skeletal muscle cells.

Other experiments were also performed with reduced incubation times. PALP also had detectable effects on protein synthesis when simultaneous treatments of cells with PALP and radiolabeled amino acids were performed only for 5 hours, although the stimulatory effects were generally smaller compared to the effects shown in TABLE 4 (data not shown).

TABLE 4

PALP stimulates protein synthesis in CCD 966 Sk human fibroblasts.

| [$^3$H] Amino acid | [$^3$H]Free Cellular Amino Acid (dpm) | | [$^3$H]Total Cellular Protein (dpm) | |
|---|---|---|---|---|
| | None | PALP | None | PALP |
| Alanine | 4,886 ± 477 | 5,956 ± 422 | 18,797 ± 409 | 21,401 ± 562 |
| Glutamine | 7,454 ± 275 | 10,824 ± 316 | 2,032 ± 108 | 2,995 ± 128 |
| Leucine | 1,012 ± 28 | 1,316 ± 133 | 2,498 ± 25 | 3,314 ± 96 |
| Methionine | 1,026 ± 51 | 2,479 ± 159 | 2,696 ± 57 | 3,652 ± 67 |
| Proline | 2,180 ± 316 | 2,990 ± 123 | 1,969 ± 62 | 3,076 ± 72 |

Examples Illustrating that PALP May Decrease the Viability of Cancerous Cells and Increase the Viability of Non-Cancerous Cells

Example 11

Effects of PALP on Cancer Cells

Figure 2:
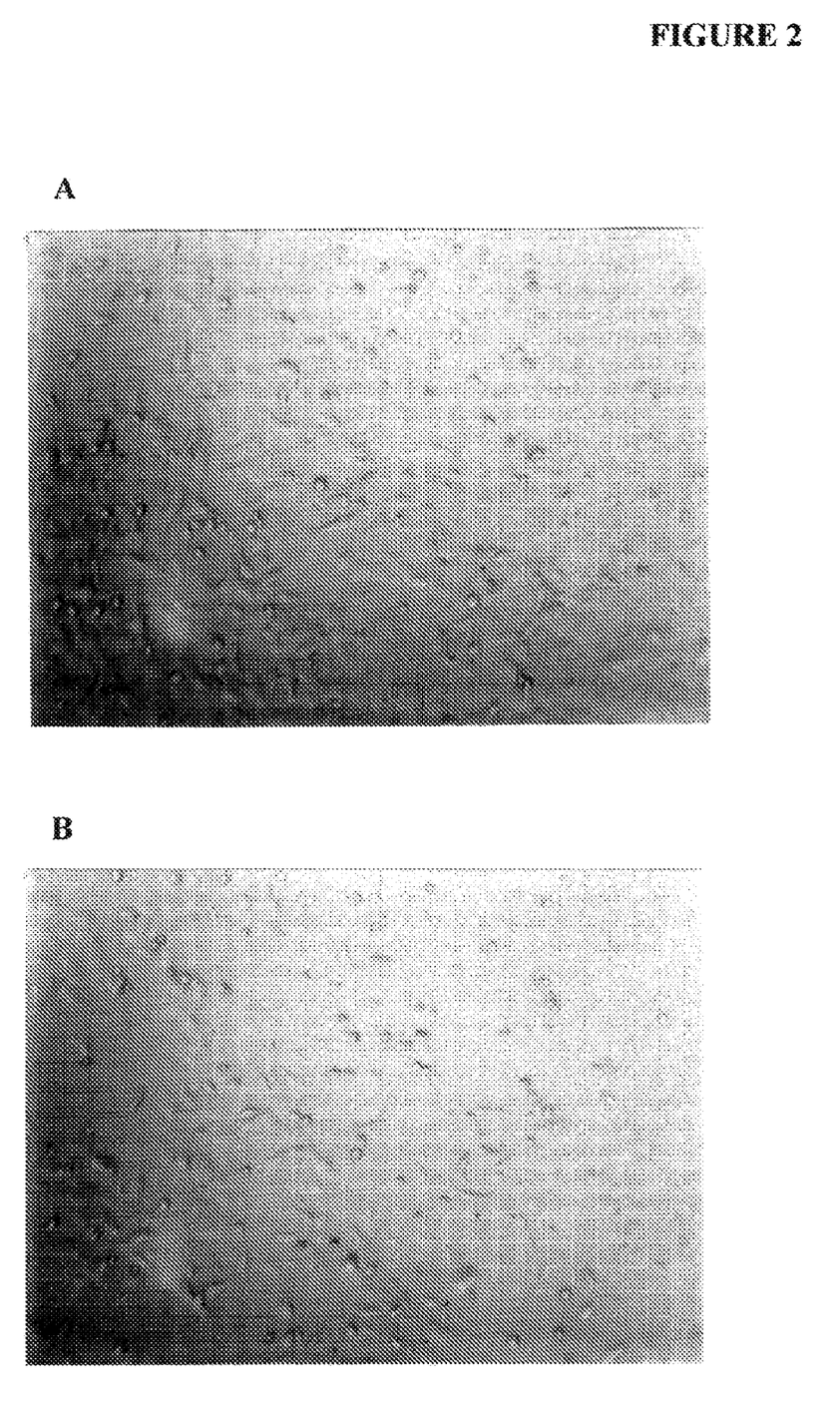
FIG. 2 shows a digital image demonstrating that incubation of Caov-3 ovarian cancer cells for 3 days in 10% serum-containing medium with 15 µg/ml purified PALP (B) visibly reduced the number of cells compared to untreated control cultures (A).
Figure 3:
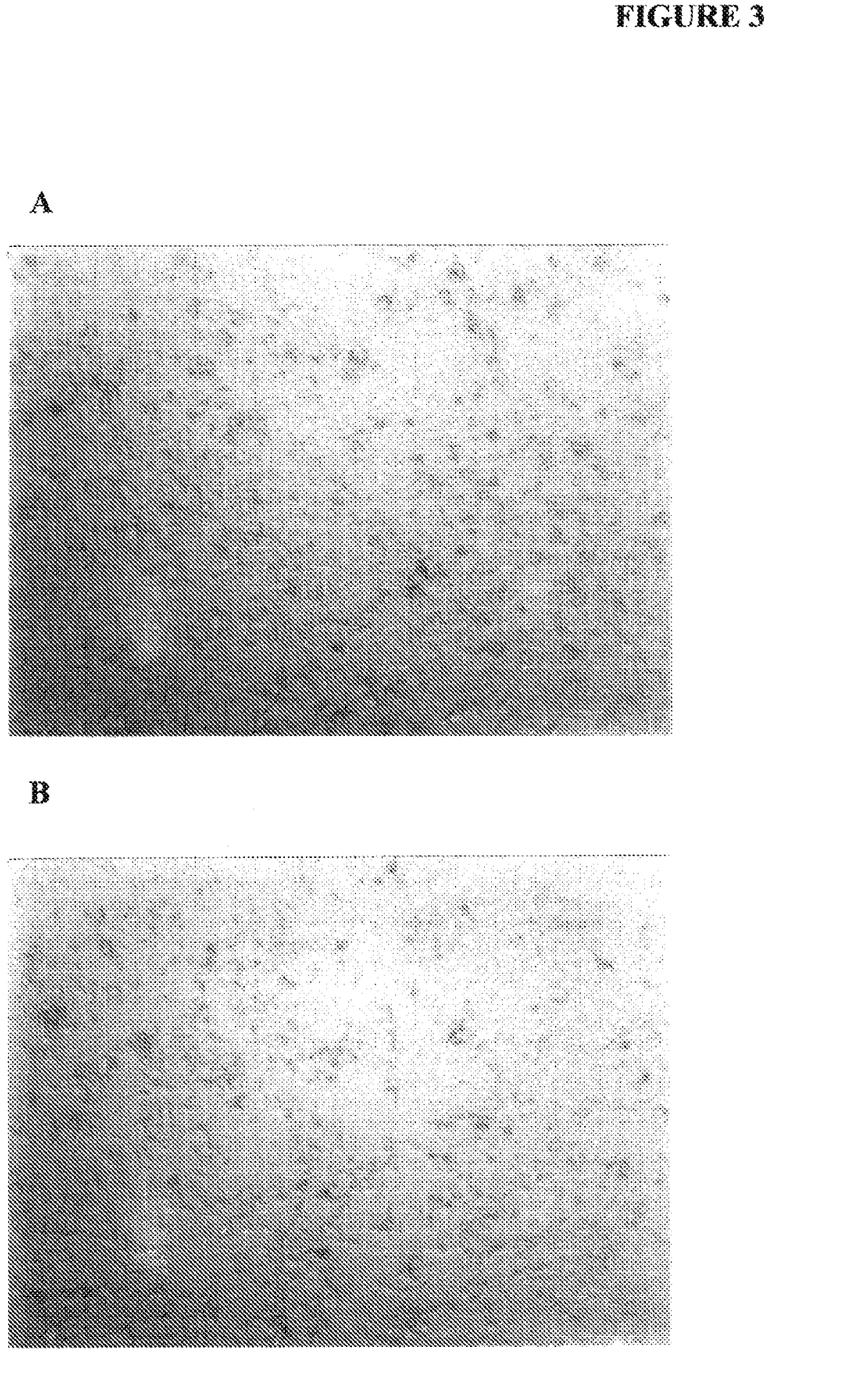
FIG. 3 shows a digital image demonstrating that incubation of AN3 CA endometrial cancer cells for 3 days in 10% serum-containing medium with 15 µg/ml purified PALP (B) reduced the number of cells about 50% compared to untreated control cultures (A).
Figure 4:
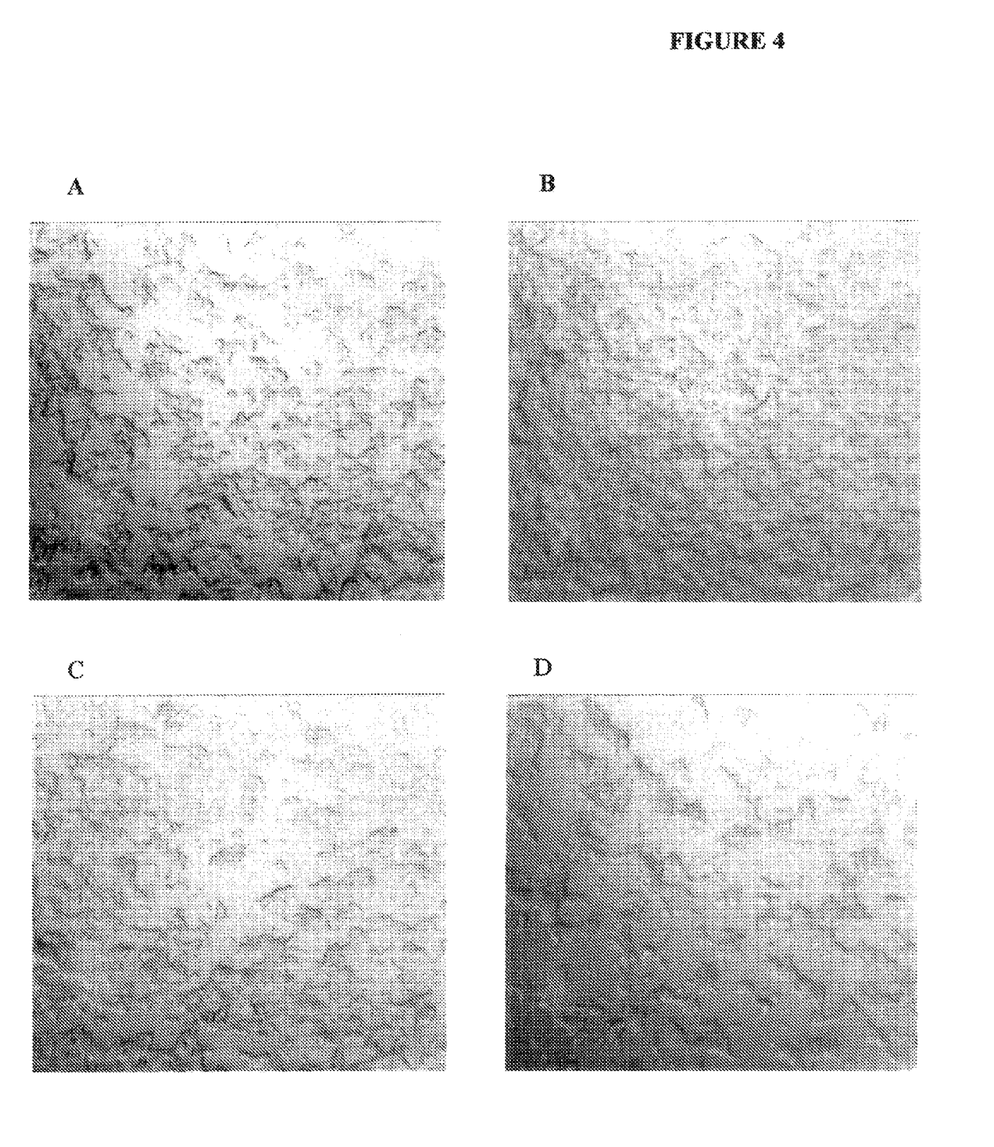
FIG. 4 shows a digital image demonstrating that incubation of ZR-75-1 breast carcinoma cells in 10% serum-containing medium from day 0 (A) until day 3 (B) increases cell density from about 50% to 100%. In the presence of 5 µg/ml purified PALP (C) and 15 µg/ml purified PALP (D) for 3 days, cells reach only about 50-60% and 30-40% confluence, respectively.

Several different types of cancer cells were treated with PALP in 10% serum-containing medium to determine if this protein might negatively affect their proliferation. FIG. 2 shows an image demonstrating that treatment of Caov-3 ovarian cancer cells for 3 days with 15 µg/ml purified PALP (FIG. 2B) visibly reduced the number of viable cells as compared to untreated control cultures (FIG. 2A). Treatment of AN3 CA endometrial cancer cells for 3 days with 15 µg/ml purified PALP (FIG. 3B) also reduced the number of cells about 50% in comparison to untreated control cultures (FIG. 3A). FIG. 4 shows another image demonstrating that incubation of ZR-75-1 human breast carcinoma cells in 10% serum-containing medium from day 0 (FIG. 4A) until day 3 (FIG. 4B) increased cell density from about 50% to 100%. However, treatment of cells with 5 µg/ml purified PALP (FIG. 4C) and 15 µg/ml purified PALP (FIG. 4D) for 3 days reduced the confluence to about 50-60% and 30-40%, respectively. Similar results were obtained with two other human breast carcinoma cell lines as discussed below.

Figure 5:
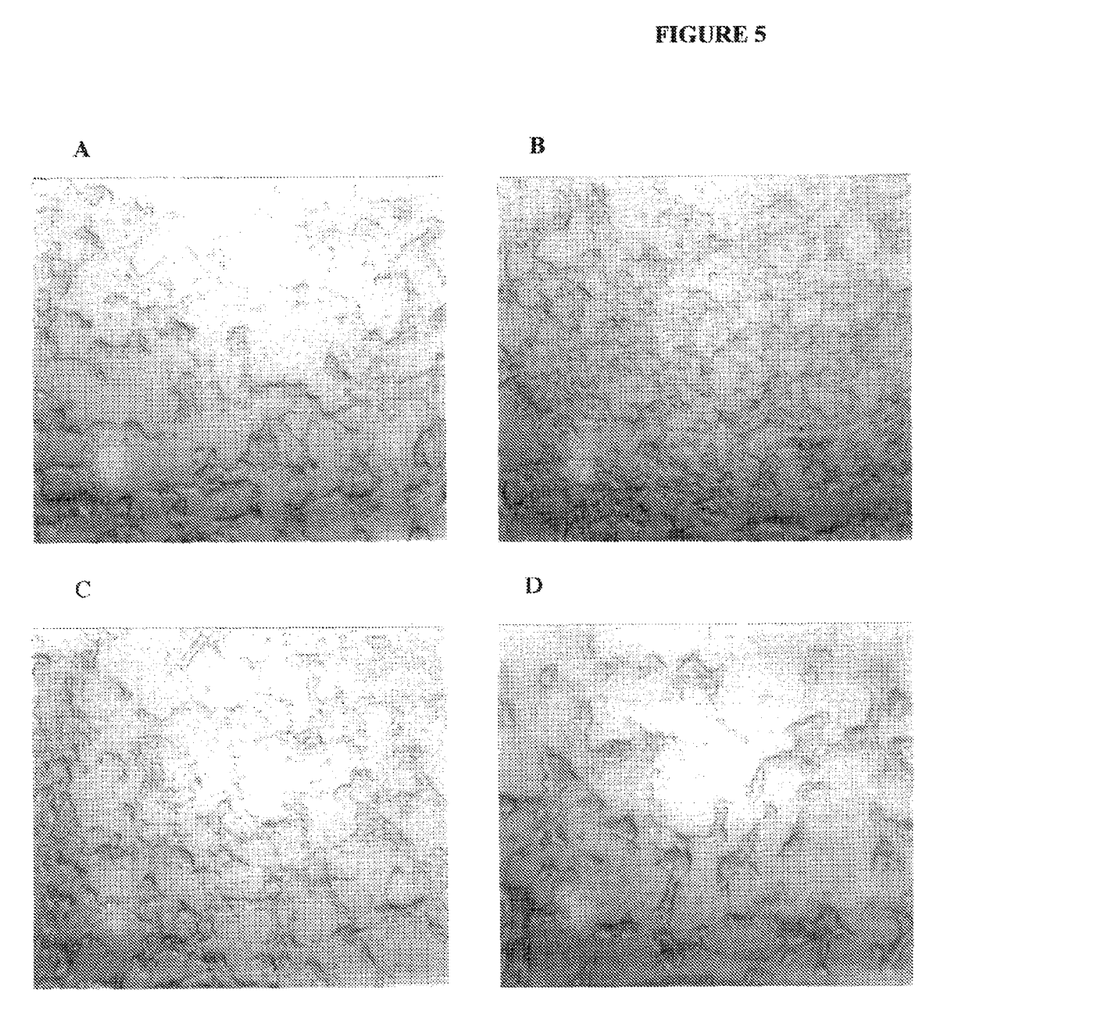
FIG. 5 shows a digital image demonstrating that incubation of T47D breast carcinoma cells in 10% serum-containing medium from day 0 (A) until day 4 (B) increases cell density from about 30-40% to 70-80%. In the presence of 5 µg/ml purified PALP (C) and 15 µg/ml purified PALP (D) for 4 days, cells reach only about 50% and 20-30% confluence, respectively.

FIG. 5 shows an image demonstrating that incubation of T47D breast cancer cells in the absence of PALP from day 0 (FIG. 5A) until day 4 (FIG. 5B) increased cell density from about 30-40% to 70-80%. However, treatments with 5 µg/ml purified PALP (FIG. 5C) and 15 µg/ml purified PALP (FIG. 5D) for 4 days reduced the confluence of T47D cells to about 50% and 20-30%, respectively.

Figure 6:
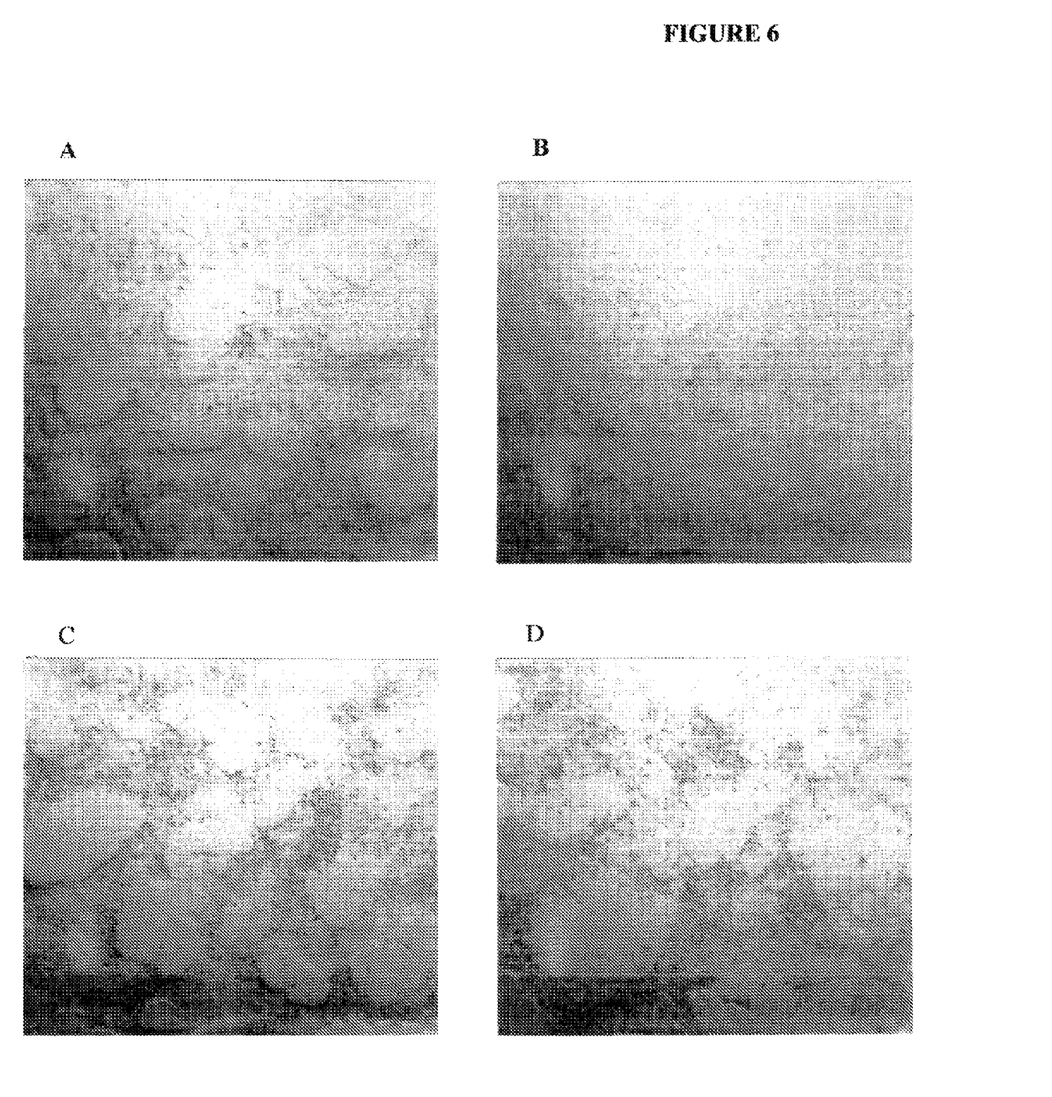
FIG. 6 shows a digital image demonstrating that incubation of MCF-7 breast carcinoma cells in 10% serum-containing medium from day 0 (A) until day 4 (B) increases cell density from about 70-% to 100%. In the presence of 5 µg/ml purified PALP (C) and 15 µg/ml purified PALP (D) for 4 days, cells reach only about 50% and 20-30% confluence, respectively.

FIG. 6 shows yet another image demonstrating that incubation of MCF-7 breast carcinoma cells in the absence of PALP from day 0 (FIG. 6A) until day 4 (FIG. 6B) increased cell density from about 70% to 100%. Again, treatments with 5 µg/ml purified PALP (FIG. 6C) and 15 µg/ml purified PALP (FIG. 6D) for 4 days reduced the confluence of MCF-7 cells to about 50% and 20-30%, respectively.

Figure 7:
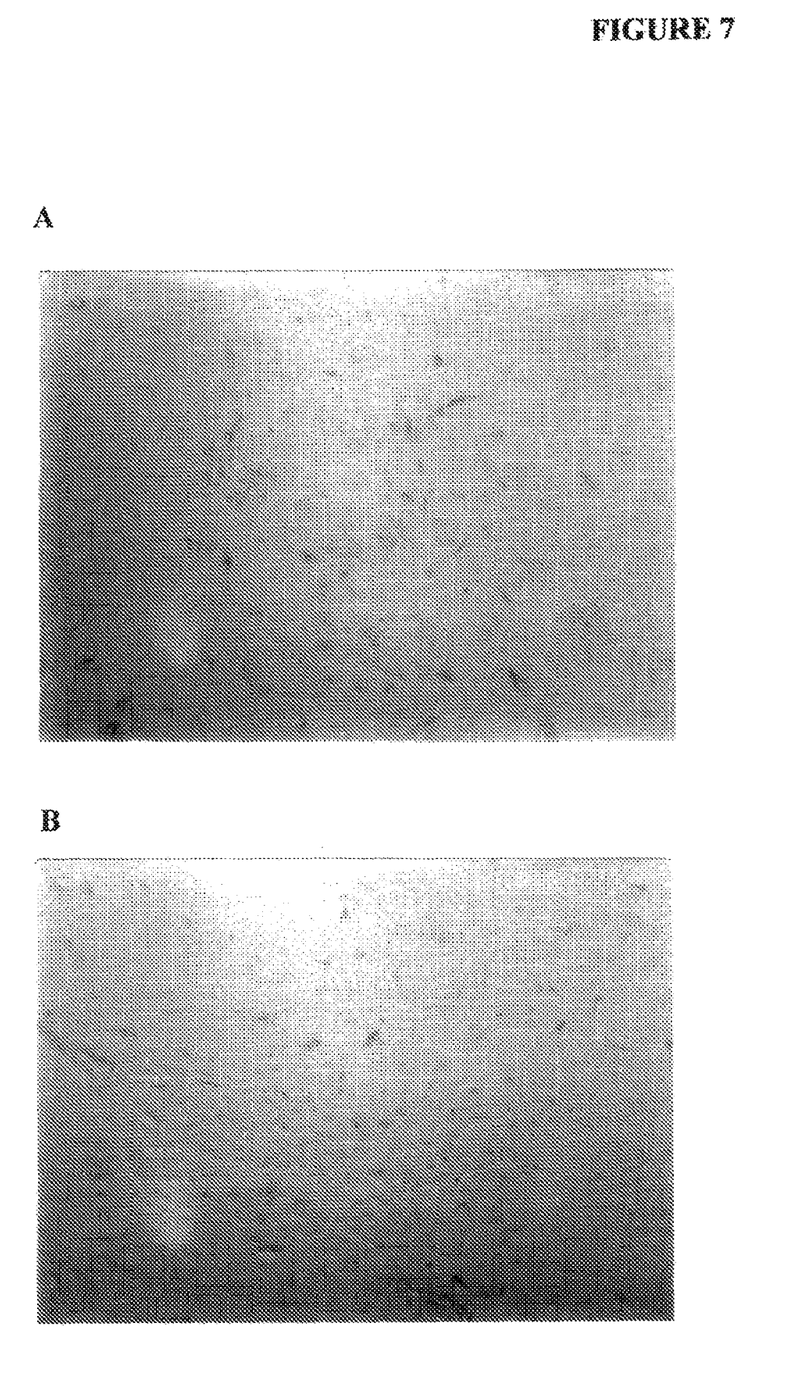
FIG. 7 shows a digital image demonstrating that while continuous incubation of MCF-10A human mammary gland (non-cancerous) cells for 12 days in 10% serum-containing medium causes the death of practically all cells (A), the presence of 15 µg/ml purified PALP promotes survival of a large number of cells (B).

MCF-10A cells were used to determine the effect of PALP under the condition of limiting nutrient supply. MCF-10A cells are non-cancerous cells that are widely used models to understand how normal mammary epithelial cells respond to chemotherapy and other treatments. MCF-10A cells were incubated for 12 days with or without PALP in 10% serum-containing medium without medium change. FIG. 7 shows an image demonstrating that continuous incubation of MCF-10A cells for 12 days in the absence of PALP (FIG. 7A) caused the death of practically all cells. In contrast, in the presence of 15 µg/ml purified PALP (FIG. 7B), a large number of cells survived. Since PALP generally decreased and enhanced the viability of cancerous and non-cancerous cells, respectively, this protein may not only decrease the viability of estrogen positive breast and other cancer cells, but it may also help to enhance the survival of the normal tissue surrounding the tumor tissue.

Examples Showing that Both Purified and Commercial PALP May Decrease the Loss of Body Weight Due to Weight Loss Inducing Therapies.

Example 12

Effect of Commercial PALP on the Body Weight of Streptozotocin (STZ)-Treated Mice In this experiment, the body weights of animals were measured to determine whether unpurified commercial PALP reduces the body weight loss in STZ-treated animals. STZ induces muscle atrophy and reduction of adipose tissue mass via ROS and is therefore a model for chemotherapeutic side-effects. STZ also induces the death of insulin-producing β-cells. One group of $BDF_1$ male mice received 1.5-mg unpurified commercial PALP intraperitoneally 72 hours prior to intraperitoneal application of 250 mg/kg of STZ on day 0. A second group of animals received only the same amount of PALP, while a third group of animals received only the same amount of STZ. A fourth group of animals received no treatment. Each group consisted of 5 animals. Body weight was measured regularly. The data, shown in TABLE 5, are expressed as mean values ±std. dev. of 5 independent determinations. Treatments with PALP in the first and second groups were repeated on the 2nd, 5th, 8th and 11th days after the addition of STZ. The results indicate that untreated animals gained about 2 g from day 0 until day 16. Animals treated with STZ alone experienced a significant loss of body weight starting on about day 2. In contrast, in mice treated with PALP, in addition to STZ, the loss of body weight decreased. Significantly, the body weight of the mice treated with PALP, in addition to STZ, did not change between day 11-16, indicating a long lasting effect of this PALP preparation.

TABLE 5

Commercial PALP protects $BDF_1$ mice against STZ-induced loss of body weight.

| | Body weights (g) | | | |
|---|---|---|---|---|
| Day | Untreated (control) | PALP alone | STZ alone | STZ + PALP |
| 0 | 28.4 ± 0.72 | 28.7 ± 0.68 | 28.3 ± 0.68 | 27.9 ± 1.16 |
| 2 | 29.2 ± 0.65 | 28.9 ± 0.70 | 24.3 ± 0.31 | 27.6 ± 1.12 |
| 4 | 29.8 ± 0.82 | 28.8 ± 0.42 | 22.6 ± 0.75 | 28.6 ± 1.14 |
| 8 | 29.7 ± 0.69 | 29.1 ± 0.63 | 21.4 ± 1.02 | 27.9 ± 0.67 |
| 11 | 30.2 ± 0.81 | 28.9 ± 0.72 | 21.1 ± 1.23 | 28.1 ± 0.83 |

TABLE 5-continued

Commercial PALP protects $BDF_1$ mice against STZ-induced loss of body weight.

| | Body weights (g) | | | |
|---|---|---|---|---|
| Day | Untreated (control) | PALP alone | STZ alone | STZ + PALP |
| 14 | 30.3 ± 0.89 | 29.7 ± 0.64 | 21.0 ± 0.93 | 27.3 ± 1.00 |
| 16 | 30.4 ± 0.96 | 29.5 ± 0.87 | 20.2 ± 0.86 | 27.9 ± 0.61 |

Example 13

Effect of Purified PALP on the Body Weight of STZ-Treated Mice

In this experiment, the body weights of animals were measured to determine whether highly purified PALP also reduces the weight loss in STZ-treated animals. One group of $BDF_1$ male mice received 0.35-mg of highly purified PALP intraperitoneally 24 hours prior to intraperitoneal application of 250 mg/kg of STZ on day 0. A second group of animals received only STZ. Finally, a third group of animals received no treatment. Treatments with PALP in the first group were repeated on the 2nd and 5th days after the addition of STZ. Each group consisted of 6 animals. Body weight was measured regularly. The data, shown in TABLE 6, are expressed as mean values ±std. dev. of 6 independent determinations. The results indicate that untreated animals gained about 3 g from day 0 to day 11. Animals treated with STZ alone experienced a loss of body weight starting on about day 2. However, administration of highly purified PALP significantly decreased STZ-induced loss in body weight. The effect of highly purified PALP was also shown to be long lasting evidenced by the increase in weight of PALP+STZ-treated animals between the days of last PALP treatment (day 5) and conclusion of the experiment (day 11).

TABLE 6

Purified PALP protects $BDF_1$ mice against STZ-induced loss of body weight.

| | Body weights (g) | | |
|---|---|---|---|
| Day | Untreated (control) | STZ alone | STZ + PALP |
| 0 | 27.3 ± 0.58 | 28.5 ± 0.42 | 28.3 ± 0.52 |
| 2 | 28.4 ± 0.50 | 24.7 ± 0.39 | 27.9 ± 0.54 |
| 5 | 28.9 ± 0.59 | 22.5 ± 0.60 | 26.9 ± 0.47 |
| 7 | 29.3 ± 0.61 | 21.2 ± 0.57 | 27.1 ± 0.51 |
| 9 | 29.5 ± 0.59 | 20.9 ± 0.60 | 28.2 ± 0.60 |
| 11 | 30.6 ± 0.64 | 20.6 ± 0.47 | 28.4 ± 0.57 |

Examples Demonstrating that PALP Reduces Loss of Body Weight in Mice Caused by Implanted Tumor and Chemotherapy.

Example 14

PALP Enhances Body Weight and Survival of Human Melanoma Bearing SCID Mice

HT-168 human melanoma tumors were developed in first generation hybrid BDF1 (C57 B1 female×DBA/2 male) adult female mice kept at specified pathogen free (SPF) hygienic level. In this experiment, one group of animals were untreated, while a second group of animals were treated with 1.5 mg of partially purified PALP preparation containing about 65% PALP and 35% $\alpha_1$-antitrypsin. Treatment occurred on day 0, which was 17 days after inoculation of tumor cells. Each of these groups contained 5 mice. PALP was administered subcutaneously. Treatments with PALP were performed 5 times a week for 3 weeks. The total weight of animals and tumor size was measured regularly. Over the course of entire treatment, PALP appeared to decrease tumor size by 16-22%, but these changes did not have statistical significance (data not shown). PALP also increased the average survival time from 43.6±11.6 to 64.0±13.0 days. The data showing changes in total weight are found in TABLE 7. These data are expressed as mean values ±std. dev. of 5 independent determinations. The results indicate that animals treated with PALP gained more weight than control animals. By day 23, the tumor size in the groups of untreated and PALP treated animals was 4.2±1.14 cm$^3$ and 3.36±0.57 cm$^3$, respectively. Taking the tumor size into account, control animals actually lost about 1.5 g body weight (if the tumor weight is excluded from the total weight), while PALP-treated animals gained 0.9 g body weight. [Note that 1 cm$^3$ volume of tissue equals 0.7 g weight].

Since in mice, like in any other mammal, muscle and adipose tissue constitute a significant portion of body weight, prevention of loss of body weight in PALP-treated mice was possible only if there was no significant loss in the mass of muscle and adipose tissue.

TABLE 7

PALP increases total weight of melanoma bearing mice.

| Day | Total weight of animals (g) | |
|---|---|---|
| | Untreated (Control) | PALP-treated |
| 0 | 20.1 ± 0.66 | 20.7 ± 0.89 |
| 4 | 19.5 ± 0.61 | 21.6 ± 0.75 |
| 9 | 19.9 ± 0.98 | 22.2 ± 0.69 |
| 14 | 20.8 ± 0.78 | 23.1 ± 0.81 |
| 19 | 20.9 ± 1.00 | 24.1 ± 1.03 |
| 23 | 21.6 ± 0.96 | 24.0 ± 1.12 |

Example 15

PALP Enhances Body Weight and Survival of Human Prostate Cancer Bearing SCID Mice PC-3 human prostate tumors were developed in first generation hybrid BDF1 (C57 B1 female×DBA/2 male) adult female mice kept at specified pathogen free (SPF) hygienic level. One group of animals were untreated, while a second group of animals were treated with 1.5 mg of partially purified PALP preparation containing about 65% PALP and 35% $\alpha_1$-antitrypsin. Treatment occurred on day 0, which was 13 days after inoculation of tumor cells. PALP was administered subcutaneously. Each group included 7 mice. Treatments with PALP were performed 5-times a week for 3 weeks. Total weight of animals and tumor size was measured regularly. Over the treatment period, PALP decreased tumor size by 12-16%, however these changes were not statistically significant (data not shown). PALP also increased the average survival time from 37.4±10.2 to 49.4±9.6 days. The data showing the changes in total weight are found in TABLE 8. These data are expressed as mean values ±std. dev. of 7 independent determinations. The results indicate that after 16 days, untreated mice lost 2.7 g total weight. Considering that on day 16 the tumor size in untreated control animals was 4.68±1.20 cm$^3$, it is estimated that these animals actually lost about 6 g body weight. In comparison, the tumor size in PALP treated animals on day 16 was 4.15±0.56 cm$^3$ and these animals gained about 1.6 g total weight. Excluding the tumor weight, this indicates that PALP treated animals actually lost only about 1.3 g body weight.

TABLE 8

PALP reduces total weight loss in prostate tumor bearing mice.

| Day | Total weight of animals (g) | |
|---|---|---|
| | Untreated (Control) | PALP-treated |
| 0 | 23.5 ± 0.89 | 23.1 ± 0.55 |
| 5 | 21.7 ± 1.08 | 22.9 ± 0.54 |
| 12 | 20.4 ± 0.92 | 24.8 ± 0.74 |
| 16 | 20.8 ± 0.32 | 24.7 ± 0.68 |

Example 16

Highly Purified PALP Reverses Cisplatin (CisPt)-Induced Total Weight Loss in the MXT Mammary Tumor Model The mouse mammary MXT tumor model was developed according to the method described above. On day 7 the animals were either untreated (Group 1) or were treated with 3 mg/kg of CisPt (Group 2) or 3 mg/kg of CisPt+0.3 mg/mouse of highly purified PALP (Group 3). The results are shown in TABLE 9. In another experiment the same treatments were performed except that the injected amount of highly purified PALP was 0.4 mg per mouse. These results are shown in TABLE 10. In both experiments, CisPt and PALP were administered intraperitoneally and subcutaneously, respectively, 5-times every second day. Total weight of animals and tumor size was measured regularly. Over the course of entire treatment, CisPt decreased tumor weight by 42-58%, and PALP at 0.3 mg/mouse and 0.4 mg/mouse concentrations caused further 10-16% and 18-22% decreases in tumor weight. CisPt also increased average survival time by 28-30%, and both concentrations of PALP further increased survival time by 19-21%. In both TABLE 9 and TABLE 10, the data are expressed as mean values ±std. dev. of 7 independent determinations. "Day 0" is the first day of treatment with PALP.

As shown in TABLE 9, in the first experiment CisPt decreased the total weight of animals from 27.5 g to 20.3 g by day 11. In mice receiving a 0.3 mg per animal dose of PALP, CisP-induced total weight loss was reduced by about 55%.

As shown in TABLE 10, in the second experiment CisPt decreased the total weight of animals from 26.7 g to 20.1 g by day 11. However, in mice receiving a 0.4 mg dose of PALP, CisPt-induced total weight loss was greatly reduced. During the same period, CisPt and CisPt+PALP reduced the tumor size from 9.18 cm$^3$ to 5.39 and 4.18 cm$^3$, respectively.

It should also be noted that during the 11 days in the second experiment, untreated animals gained 4.4 g total weight. However, considering the gain in tumor size, untreated animals actually lost about 4.5 g body weight (excluding tumor weight). CisPt-treated animals lost 2.2 g total weight during 11 days. Considering the average size of tumors in these animals, CisPt treatment resulted in the loss of about 7 g body weight (excluding tumor weight). CisPt+PALP-treated animals gained about 3.9 g total weight during the 11 day period.

Again, considering the average size of tumors, simultaneous treatment with CisPt+PALP caused practically no loss of body weight (excluding tumor weight). Overall, these experiments strongly indicate that treatment with an effective amount of PALP (0.4 mg/mouse or 16 mg/kg, in this tumor model) can reverse the loss of body weight induced by large tumors and chemotherapy.

Chemotherapy is known to induce breakdown of muscle proteins and thereby decrease muscle mass. Previous data demonstrating the stimulatory effects of PALP on protein synthesis in muscle cells combined with the protective effects of PALP against chemotherapy-induced loss of body weight strongly suggest that in the CisPt-treated MXT tumor model as well PALP prevented the loss of muscle mass.

Since PALP is a human-specific protein, it is likely to be less effective in mice than in humans for two reasons. First, human cells are expected to be more sensitive to the actions of a human protein compared to mouse-derived cells. Second, mice, unlike humans, will develop neutralizing antibody against human PALP which is expected to greatly decrease its effectiveness. Therefore, in humans, significantly less PALP may be required to elicit these protective effects on muscle and adipose tissue mass.

TABLE 9

Purified PALP at the 0.3-mg per mouse dose partially protects mice against CisPt-induced loss of total weight.

| | Total weight of animals (g) | | |
|---|---|---|---|
| Day | Untreated (control) | CisPt | CisPt + PALP |
| 0 | 22.6 ± 0.59 | 22.8 ± 0.47 | 22.3 ± 0.50 |
| 4 | 24.4 ± 0.72 | 22.7 ± 0.50 | 22.9 ± 0.44 |
| 6 | 25.0 ± 0.80 | 21.9 ± 0.68 | 23.0 ± 0.75 |
| 8 | 26.3 ± 0.89 | 20.8 ± 0.82 | 23.9 ± 1.01 |
| 11 | 27.5 ± 0.82 | 20.3 ± 0.71 | 24.4 ± 0.26 |

TABLE 10

Purified PALP at the 0.4-mg per mouse dose almost fully protects mice against CisPt-induced loss of total weight.

| | Total Weight of animals (g) | | |
|---|---|---|---|
| Day | Untreated (control) | CisPt | CisPt + PALP |
| 0 | 22.3 ± 0.61 | 22.5 ± 0.37 | 22.1 ± 0.52 |
| 4 | 24.6 ± 0.91 | 23.1 ± 0.52 | 24.2 ± 0.27 |
| 6 | 25.4 ± 0.93 | 21.7 ± 0.45 | 25.4 ± 0.25 |
| 8 | 25.9 ± 1.13 | 20.9 ± 0.65 | 25.6 ± 0.36 |
| 11 | 26.7 ± 1.31 | 20.1 ± 1.05 | 26.0 ± 0.33 |

What is claimed is:

1. A method of decreasing the loss of body weight and muscle mass in a mammal wherein the loss of body weight and muscle mass is caused by cancer, the method including administering an alkaline phosphatase or an active derivative thereof.

2. The method of claim 1, wherein the mammal is a human.

3. The method of claim 1, wherein the alkaline phosphatase is placental alkaline phosphatase.

4. The method of claim 1, wherein the alkaline phosphatase is obtained by extraction from natural sources such as blood, kidney, liver, testis, intestine, or placental tissue.

5. The method of claim 1, wherein the alkaline phosphatase or an active derivative is obtained by recombinant methods.

6. The method of claim 1, wherein the alkaline phosphatase or an active derivative is obtained by chemical synthesis.

7. The method of claim 1, wherein placental alkaline phosphatase is administered via injection chosen from intravenous, intraperitoneal, subcutaneous, intraarterial, intradermal, intraportal or intramuscular delivery routes.

8. The method of claim 1, wherein the mammal is administered a dose of about 0.01-2.5 g of alkaline phosphatase per $m^2$ body surface of the mammal.

9. The method of claim 1, wherein the alkaline phosphatase is administered once a week, three-times a week, or every day.

10. A method of claim 1, wherein the patient is also administered a body weight loss-inducing therapy.

11. The method of claim 10, wherein the body weight loss-inducing therapy is a chemotherapy including cisplatin, doxorubicin, mytomycin C or etoposide therapy.

12. A method of decreasing the loss of body weight and muscle mass in a mammal with cancer that is being treated with a chemotherapeutic drug, the method including administering an alkaline phosphatase or an active derivative thereof.

13. The method of claim 12, wherein the mammal is a human.

14. The method of claim 12, wherein the alkaline phosphatase is placental alkaline phosphatase.

15. The method of claim 12, wherein placental alkaline phosphatase is administered via injection chosen from intravenous, intraperitoneal, subcutaneous, intraarterial, intradermal, intraportal or intramuscular delivery routes.

16. The method of claim 12, wherein the mammal is administered a dose of about 0.01-2.5 g of alkaline phosphatase per $m^2$ body surface of the mammal.

17. The method of claim 12, wherein the alkaline phosphatase is administered once a week, three-times a week, or every day.

* * * * *